US009655756B2

(12) United States Patent
LeBlanc et al.

(10) Patent No.: US 9,655,756 B2
(45) Date of Patent: May 23, 2017

(54) SYSTEMS AND METHODS FOR DEPLOYING A PORTION OF A STENT USING AN AUGER-STYLE DEVICE

(71) Applicant: Cook Medical Technologies LLC, Bloomington, IN (US)

(72) Inventors: Johnny LeBlanc, Bloomington, IN (US); William J. Havel, West Lafayette, IN (US); Siddharth Vad, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 419 days.

(21) Appl. No.: 14/105,921

(22) Filed: Dec. 13, 2013

(65) Prior Publication Data
US 2014/0180384 A1 Jun. 26, 2014

Related U.S. Application Data

(60) Provisional application No. 61/745,171, filed on Dec. 21, 2012.

(51) Int. Cl.
A61F 2/966 (2013.01)
A61F 2/95 (2013.01)

(52) U.S. Cl.
CPC ............ A61F 2/966 (2013.01); A61F 2/95 (2013.01); A61F 2002/9505 (2013.01)

(58) Field of Classification Search
CPC ..... A61F 2002/9505; A61F 2/95; A61F 2/966
See application file for complete search history.

(56) References Cited

U.S. PATENT DOCUMENTS 4,732,154 A * 3/1988 Shiber .............. A61B 17/22012
606/108
5,078,723 A * 1/1992 Dance ................ A61B 17/3207
604/22
5,201,757 A 4/1993 Heyn et al.
5,480,423 A 1/1996 Ravenscroft et al.
5,626,604 A * 5/1997 Cottone, Jr. ............ A61F 2/958
606/1

(Continued)

FOREIGN PATENT DOCUMENTS

DE 102006053748 4/2008
EP 1440673 7/2004

(Continued)

OTHER PUBLICATIONS

Response to Extended European Search Report for Application No. 13197539.3 filed Dec. 16, 2014, 11 pgs.

(Continued)

Primary Examiner — Julie A Szpira
(74) Attorney, Agent, or Firm — Brinks Gilson & Lione

(57) ABSTRACT

The present embodiments provide systems and methods for deploying at least a portion of a stent. In one embodiment, the system comprises a cannula having an outer surface, and an auger having a plurality of turns coupled to the outer surface of the cannula. A stent has a portion dimensioned to be disposed within a valley of the auger. Rotation of the cannula and the auger advances the portion of the stent in a predetermined longitudinal direction.

13 Claims, 3 Drawing Sheets

(56) References Cited

U.S. PATENT DOCUMENTS

| | | | |
|---|---|---|---|
| 5,653,722 A * | 8/1997 | Kieturakis | A61B 17/00008 606/159 |
| 5,776,142 A * | 7/1998 | Gunderson | A61F 2/88 606/108 |
| 5,824,041 A | 10/1998 | Lenker et al. | |
| 5,824,058 A | 10/1998 | Ravenscroft | |
| 6,077,296 A | 6/2000 | Shokoohi et al. | |
| 6,379,334 B1 * | 4/2002 | Frassica | A61B 1/015 604/164.07 |
| 6,872,224 B1 | 3/2005 | Telxelra Moretra et al. | |
| 7,101,390 B2 | 9/2006 | Nelson | |
| 7,147,657 B2 | 12/2006 | Chiang | |
| 7,264,632 B2 | 9/2007 | Wright | |
| 7,297,156 B2 | 11/2007 | Nelson | |
| 7,335,224 B2 | 2/2008 | Ohlenschlaeger | |
| 7,611,528 B2 | 11/2009 | Goodson, IV | |
| 7,632,298 B2 | 12/2009 | Hijlkema et al. | |
| 7,815,671 B2 | 10/2010 | Wright et al. | |
| 7,909,863 B2 | 3/2011 | Hartley et al. | |
| 7,942,924 B1 | 5/2011 | Perez et al. | |
| 7,959,661 B2 | 6/2011 | Hijlkema et al. | |
| 8,043,354 B2 | 10/2011 | Greenberg et al. | |
| 8,062,345 B2 | 11/2011 | Ouellette et al. | |
| 8,109,986 B2 | 2/2012 | Styrc | |
| 8,366,674 B2 * | 2/2013 | Frassica | A61B 1/015 600/101 |
| 2005/0049674 A1 | 3/2005 | Berra et al. | |
| 2008/0264102 A1 | 10/2008 | Berra | |
| 2009/0030497 A1 | 1/2009 | Metcalf et al. | |
| 2009/0099637 A1 | 4/2009 | Barthold et al. | |
| 2009/0192585 A1 | 7/2009 | Bloom et al. | |
| 2009/0270966 A1 | 10/2009 | Douk et al. | |
| 2009/0287299 A1 | 11/2009 | Tabor et al. | |
| 2009/0306761 A1 | 12/2009 | Hebert et al. | |
| 2010/0010617 A1 | 1/2010 | Goodson, IV et al. | |
| 2010/0125323 A1 * | 5/2010 | Berglund | A61F 2/88 623/1.11 |
| 2010/0249896 A1 | 9/2010 | Sugimoto et al. | |
| 2010/0324647 A1 | 12/2010 | Rincon | |
| 2011/0251664 A1 | 10/2011 | Acevedo | |
| 2012/0010696 A1 | 1/2012 | Greenberg et al. | |

FOREIGN PATENT DOCUMENTS

| | | |
|---|---|---|
| EP | 2266509 | 8/2013 |
| JP | 2002-291756 | 10/2002 |
| WO | 2000/065270 | 11/2000 |
| WO | 2008/098255 | 8/2008 |
| WO | 2009/098255 | 8/2009 |
| WO | WO2010/056522 | 5/2010 |

OTHER PUBLICATIONS

European Search Report for Application No. 13171753 dated Oct. 21, 2013, 7 pgs.

European Search Report for Application No. 10166254 mailed Oct. 31, 2010, 2 pgs.

Extended European Search Report for Application No. 13197539.3 dated Apr. 28, 2014, 7 pgs.

* cited by examiner

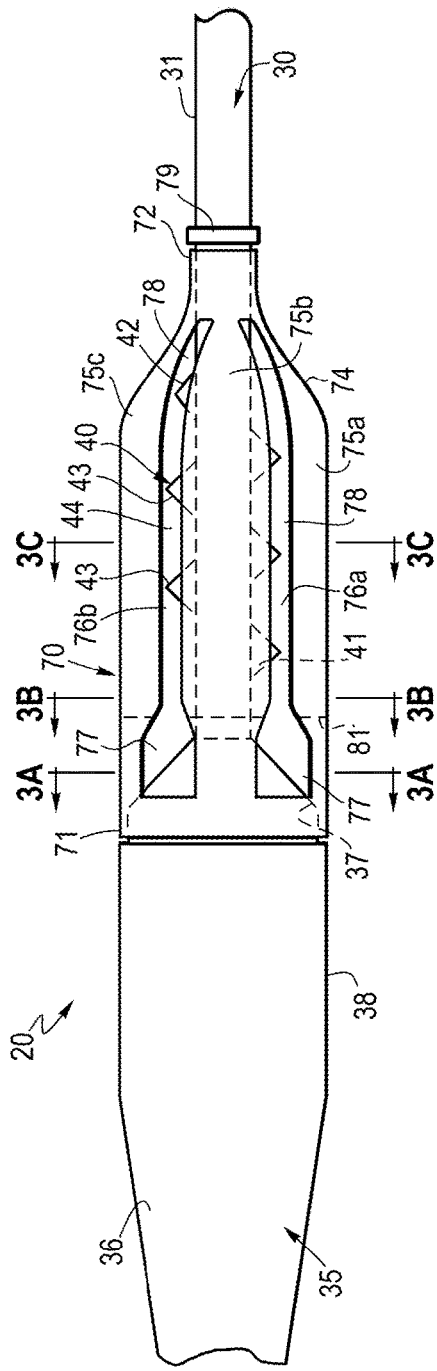
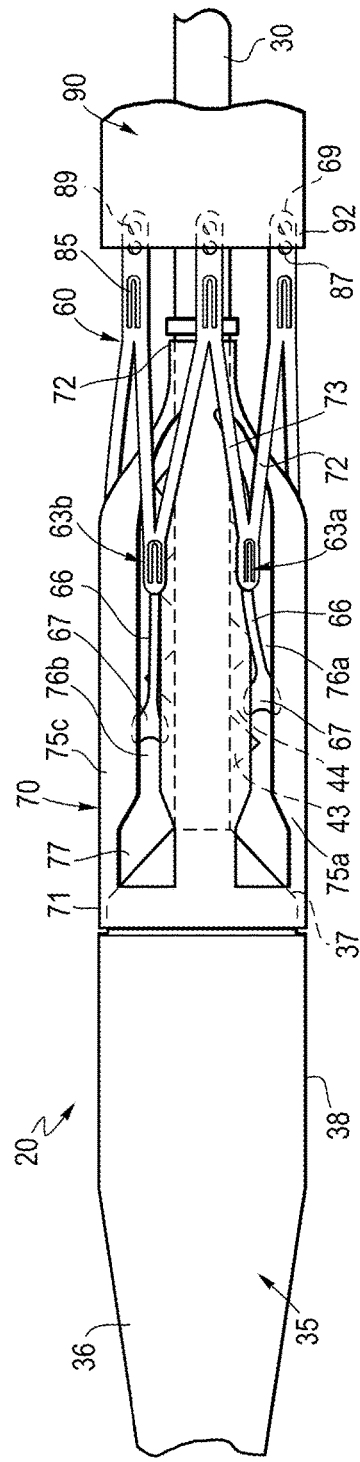

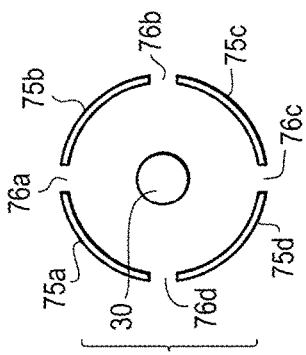
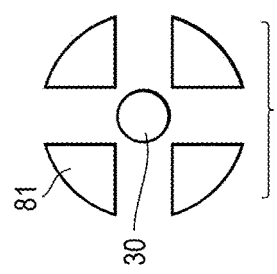
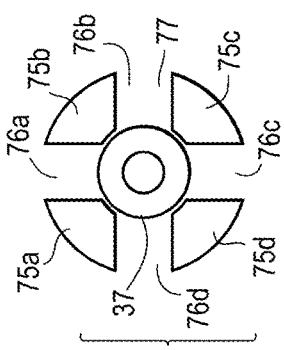
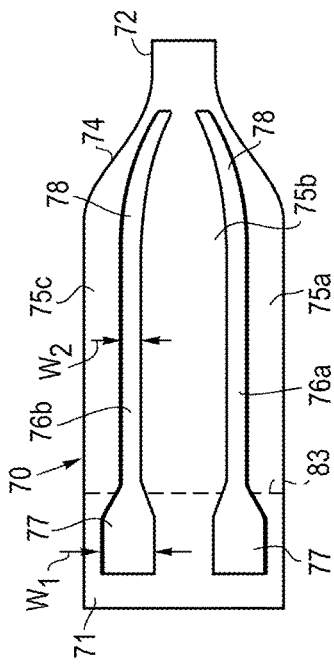
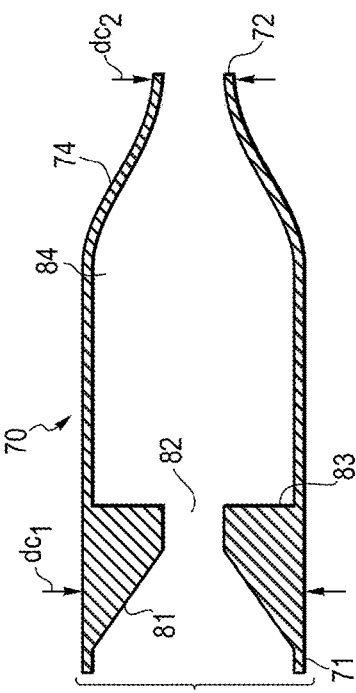

SYSTEMS AND METHODS FOR DEPLOYING A PORTION OF A STENT USING AN AUGER-STYLE DEVICE

PRIORITY CLAIM

This invention claims the benefit of priority of U.S. Provisional Application Ser. No. 61/745,171, entitled "Systems and Methods for Deploying a Portion of a Stent Using and Auger-Style Device," filed Dec. 21, 2012, the disclosure of which is hereby incorporated by reference in its entirety.

BACKGROUND

The present embodiments relate generally to apparatus and methods for treating medical conditions, and more specifically, to systems and methods for deploying a portion of a stent using an auger-style device.

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

When trigger wires are used as a deployment control mechanism, the trigger wires may releasably couple the proximal and/or distal ends of a stent or stent-graft to a delivery catheter. Typically, one or more trigger wires are looped through a portion of the stent near a vertex of the stent. For example, trigger wires may be used to restrain a "Z-stent" or Gianturco stent comprising a series of substantially straight segments interconnected by a series of bent segments. The trigger wires may be disposed through, and pull upon, the bent segments to pull the stent closely against the delivery catheter.

Trigger wires also may be used in conjunction with different stent designs, such as cannula-cut stents having relatively acute or pointed bends. The designs of cannula-cut stents may facilitate compression of the stent to a relatively small delivery profile due to the tight bends of the apices. With such stents, the trigger wires may be looped around one or more vertices formed beneath the proximal and/or distal apices, e.g., a location where an individual apex splits into two separate strut segments.

If trigger wires are threaded through the vertices of such cannula-cut stents, the trigger wires may become crimped at the vertices during compression of the stent to a reduced diameter delivery profile. If the trigger wires are crimped between the strut segments, the trigger wires and/or stent segments may become damaged during delivery, particularly for nickel-titanium stents that may be sensitive to surface imperfections. Furthermore, in some instance, trigger wires may require a relatively high deployment force when being retracted, and the provision of multiple trigger wires may add to the profile of the delivery system.

SUMMARY

The present embodiments provide systems and methods for deploying at least a portion of a stent. In one embodiment, the system comprises a cannula having an outer surface, and an auger having a plurality of turns coupled to the outer surface of the cannula. A stent has a portion dimensioned to be disposed within a valley of the auger. Rotation of the cannula and the auger advances the portion of the stent in a predetermined longitudinal direction.

An enclosure may encircle the auger. The enclosure may comprise a plurality of struts separated by a plurality of slots, where the portion of the stent extends through one of the plurality of slots in a delivery state. In one example, each of the plurality of struts and each of the plurality of slots are generally parallel to each other in a direction running along a longitudinal axis of the apparatus.

In one embodiment, at least one of the plurality of slots of the enclosure has proximal and distal regions and a width at the proximal region is greater than a width at the distal region. The stent may comprise a widened securement region that comprises a width that is less than a width of the proximal region of the slot and greater than a width at the distal region of the slot. The stent further may comprise a proximal extension disposed adjacent to the widened securement region, where a width of the proximal extension is less than the width of the distal region of the slot.

The enclosure may be circumferentially rotatable relative to the cannula. An atraumatic tip is coupled to the cannula, and at least a portion of the atraumatic tip may be disposed beneath the enclosure. A distal stop member coupled to the cannula may be positioned adjacent to a distal end of the enclosure and allows the enclosure to rotate relative to the cannula, but prevents the enclosure from sliding distally over the cannula.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 1 is a side view of an embodiment of a system comprising an auger and an enclosure.

FIG. 2 is a side view depicting a portion of a stent used with the system of FIG. 1.

FIGS. 3A-3C are, respectively, cross-sectional views of the apparatus of FIG. 1 as taken along lines A-A, B-B and C-C.

FIG. 4 is a side-sectional view of the enclosure of FIG. 1.

FIG. 5 is a side view of the enclosure of FIG. 1.

DETAILED DESCRIPTION OF THE PREFERRED EMBODIMENTS

Figure 6:
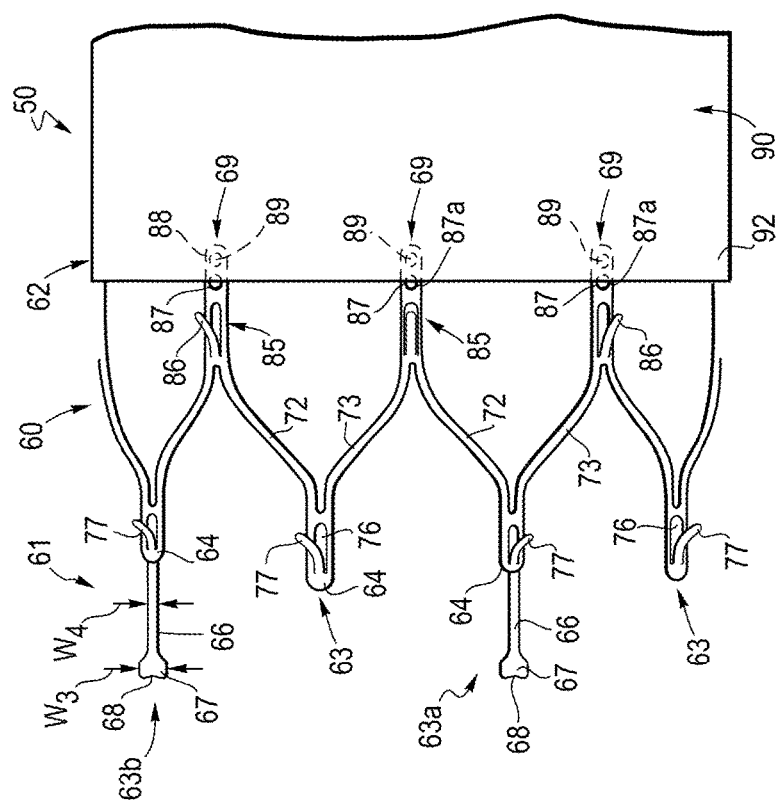
FIG. 6 depicts an exemplary stent-graft having a portion that may be deployed using the system of FIGS. 1-5.

In the present application, the term "proximal" refers to a direction that is generally closest to the heart during a medical procedure, while the term "distal" refers to a direction that is furthest from the heart during a medical procedure.

Referring to FIGS. 1-2, a first embodiment of an apparatus 20 is shown for deploying a portion of a stent. The apparatus 20 generally comprises a cannula 30 having an outer surface 31, and an auger 40 having a region that is coupled to the outer surface 31 of the cannula 30.

The cannula 30 may be incorporated as part of a broader stent or stent-graft delivery system, and may span a longitudinal length in which a distal segment extends outside of a patient's body, and a proximal segment, including the auger 40, is delivered towards a target site inside of a patient's body. The cannula 30 may be used as an inner cannula, to the extent that one or more outer cannulas or sheaths are disposed coaxially over the cannula 30. For example, a stent-graft may be disposed over an exterior surface of the cannula 30 and within one or more outer cannulas or sheaths, thereby encompassing the stent-graft during a delivery stage.

The cannula 30 may comprise a tubular member having a lumen sized to allow the cannula 30 to be advanced over a wire guide during delivery. A proximal region of the cannula 30 may be integrally formed with, or externally coupled to, an atraumatic tip 35. The atraumatic tip 35 may comprise proximal and distal regions 36 and 37, respectively, and a central region 38 disposed therebetween. The proximal and distal regions 36 and 37 comprise a smaller outer diameter relative to the central region 38, with a first taper allowing for a smooth transition between the proximal region 36 and the central region 38, and a second taper allowing for a smooth transition between the distal region 37 and the central region 38.

The auger 40 comprises a proximal end 41, a distal end 42, a plurality of helical turns 43 disposed therebetween, and valleys 44 disposed between the helical turns 43, as shown in FIGS. 1-2. As will be described further below, a portion of a stent 60 may be secured within the valleys 44 between adjacent helical turns 43.

In one non-limiting example, the auger 40 may be secured directly to the outer surface 31 of the cannula 30 using a suitable mechanism, such as a solder, weld, mechanical attachment, friction fit, or combination of these or other techniques and mechanisms. Alternatively, the auger 40 may be secured to an outer surface of a cylindrical supporting member, such as a steel tube, which in turn is securely disposed around the outer surface 31 of the cannula 30 using any of the aforementioned techniques.

The exemplary auger 40 may be formed from stainless steel, nitinol, titanium, or other suitable biocompatible materials. In one example, the auger 40 is formed from a material that has radiopaque properties.

The apparatus 20 further comprises an enclosure 70 for housing the auger 40. The enclosure 70 comprises a first end 71 having an outer diameter $dc_1$, and a second end 72 having a second outer diameter $dc_2$, as best seen in FIGS. 1 and 4. It is noted that the diameter at the first end 71 of the enclosure 70 can be larger to accommodate the provision of the helical turns 43 of the auger 40, while still providing spacing between an outermost surface of the helical turns 43 and an inner surface of the enclosure 70 to ensure that the helical turns 43 can rotate relative to the enclosure 70, as explained further below. A second end 72 of the enclosure 70 may be positioned distally of the auger 40, as shown in FIG. 1, and the second outer diameter $dc_2$ may be slightly larger than the outer surface 31 of the cannula 30. A taper 74 reduces the diameter of the enclosure 70 between the first end having the outer diameter $dc_1$ and the second end having the reduced outer diameter $dc_2$.

In the examples shown, the first end 71 of the enclosure 70 is the proximal end, while the second end 72 of the enclosure 70 is the distal end. However, in alternative embodiments, the axial orientation of the enclosure 70 may be reversed. For example, the enclosure 70 may have the first end 71 of greater diameter located distally, while the second end 72 of lesser diameter is located proximally, and a reverse rotational sequence of deployment may be used relative to the manner described herein.

The enclosure 70 further comprises a plurality of struts separated by a plurality of slots. Each of the struts and slots has proximal and distal ends, and are generally parallel to each other in a direction running along a longitudinal axis of the apparatus, as shown in FIG. 1. In this non-limiting example, four struts 75a-75d are depicted as being separated by four slots 76a-76d, as shown in FIGS. 1-2, 3A-3C and 5. However, it will be appreciated that greater or fewer number than four slots and four struts may be provided for coupling selected proximal apices of a stent 60 to the enclosure 70, as explained further below.

Each of the slots 76a-76d has proximal regions 77 and distal regions 78. The proximal regions 77 have a width $w_1$, which is greater than a width $w_2$ of the distal regions 78, as depicted in FIG. 5. The widening of the proximal regions 77 of the slots 76a-76d allows a widened securement region 67 of the stent 60 to be radially advanced only through the proximal regions 77 of their associated slots.

In particular, the widened securement region 67 comprises a width $w_3$, which is less than the width $w_1$ of the proximal regions 77 of the slots, but greater than the width $w_2$ of the distal regions 78, as indicated by the dimensions in FIGS. 5-6, and depicted in an assembled state of FIG. 2. The width $w_2$ of the distal regions 78 of the slots 76a-76d is greater than a width $w_4$ of proximal extensions 66 of the stent 60, which may be disposed adjacent to the widened securement regions 67, thereby allowing the proximal extensions 66 to extend through an associated slot, as depicted in FIG. 2.

In one embodiment, the enclosure 70 is designed to cooperate with at least a portion of the atraumatic tip 35. The distal region 37 of the atraumatic tip 35 may comprise an outer surface that corresponds to the shape of an inner surface at a proximal region of the enclosure 70. In particular, the enclosure 70 comprises a proximal inner taper 81, as shown in FIG. 4. The outer surface of the distal region 37 of the atraumatic tip 35 generally annularly abuts the proximal inner taper 81 in the assembled state of FIGS. 1-2.

In accordance with one aspect, the enclosure 70 can rotate circumferentially relative to the atraumatic tip 35 and the cannula 30. Notably, the proximal inner taper 81 of the enclosure 70 is disposed around the distal region 37 of the atraumatic tip 35, while the distal end 72 of the enclosure 70 is disposed around the outer surface 31 of the cannula 30. Since the proximal and distal regions of the enclosure 70 are not secured to the atraumatic tip 35 and the cannula 30, respectively, the enclosure 70 can rotate circumferentially relative to these components.

A distal stop member 79 may be positioned adjacent to the distal end 72 of the enclosure 70, as shown in FIG. 1. The distal stop member 79 allows the enclosure 70 to rotate relative to the cannula 30, but prevents the enclosure 70 from sliding distally over the cannula 30. The distal stop member 79 may be formed integrally with the cannula 30, or as an external component secured to the outer surface 31 of the cannula, and may comprise any suitable biocompatible material.

The proximal inner taper 81 of the enclosure 70 extends inward to an opening 82, shown in FIG. 4, which has a diameter that allows passage of the cannula 30 so that the cannula 30 can be coupled to the atraumatic tip 35. Moreover, a stepped surface 83 is provided at select locations just distal to the opening 82, as shown in FIG. 4. The stepped surface 83 may be generally perpendicular to the longitudinal axis of the cannula 30. The stepped surface 83 may be positioned in the spaces that are in-between the slots 76a-76d, as depicted in FIG. 5. In other words, the stepped surface 83 is positioned only beneath the plurality of struts 75a-75d, and therefore, does not impede advancement of struts of the stent 60 through the slots 76a-76d. The stepped surface 83 may reduce the possibility that the struts of the stent 60 become inadvertently lodged under the struts 75a-75d of the enclosure 70. Preferably, the proximal end 41 of the auger 40 is disposed immediately adjacent to the stepped surface 83 of the enclosure 70, as depicted in FIG. 1.

The enclosure 70 further comprises a main housing 84, which is disposed between the stepped surface 83 and the distal end 72, as shown in FIG. 4. The main housing 84 is sized for housing the auger 40 therein, arid has an inner diameter that remains larger than the auger along its longitudinal length, thereby permitting rotation of the auger 40 within the main housing 84.

The enclosure 70 may be formed from stainless steel, nitinol, polymers, or other suitable biocompatible materials. Moreover, the enclosure 70 may be manufactured as a single component, or multiple components that are secured together. In one embodiment, the enclosure 70 may be manufactured by forming an outer shell of material, and then inserting material that forms the proximal inner taper 81 and the stepped surface 83, and separately cutting the slots 76a-76d into the outer shell.

Referring to FIG. 6, an exemplary stent-graft 50, which may be deployed using the apparatus 20 of FIGS. 1-5, has a proximally-located stent 60 coupled to the graft material 90. In this non-limiting embodiment, the stent 60 may be manufactured from a continuous cylinder into which a pattern may be cut by a laser or by chemical etching to produce slits in the wall of the cylinder. The resulting structure may then be heat set to give it a desired final configuration.

The stent 60 has proximal and distal ends 61 and 62, a series of proximal apices 63 disposed near the proximal end 61 of the stent 60, and a series of distal apices 69 disposed near the distal end 62 of the stent 60. A plurality of strut segments 72 and 73 are disposed between the series of proximal apices 63 and the series of distal apices 69, as shown in FIG. 6. The series of proximal apices 63 are each disposed proximally beyond a proximal end 92 of the graft 90, and the series of distal apices 69 of the stent 60 are each disposed distal to the proximal end 92 of the graft 90.

In FIG. 6, each of the proximal apices 63 comprise an end region 64 having an integral barb 77 formed therein. The barb 77 may be formed by laser cutting a desired barb shape into the end regions 64. A slit 76 therefore is formed into each end region 64 after the desired barb shape is formed, as shown in FIG. 6. Once the desired barb shape is cut, a main body of the barb 77 may be bent in a radially outward direction with respect to the end region 64. The angle may comprise any acute angle, or alternatively may be substantially orthogonal or obtuse. If desired, the barb 77 may be sharpened, for example, by grinding the tip of the barb, to facilitate engagement at a target tissue site.

In FIG. 6, at least one pair of adjacent, proximal apices 63 may comprise different features. In particular, alternating proximal apices 63 terminate at the end regions 64 housing the barbs 77. However, other alternating proximal apices 63a and 63b have coupling regions extending proximally beyond the end regions 64. The coupling regions of the proximal apices 63a and 63b comprise the narrower proximal extensions 66 and the widened securement regions 67, as shown in FIG. 6. For this exemplary stent 60, a total of eight proximal apices are provided around the circumference of the stent, though only four apices are depicted in the side view of FIG. 6 for illustrative purposes. Accordingly, in the example having a total of eight proximal apices with alternating features, four of the apices around the circumference of the stent will comprise only proximal apices 63 that terminate at the end regions 64 housing the barbs 77, while the other four proximal apices will have the coupling regions comprising the narrower proximal extensions 66 and the widened securement regions 67, as depicted by the proximal apices 63a and 63b in the side view of FIG. 6. In this example, the coupling regions of the proximal apices 63a and 63b are coupled to the slots 76a and 76b of the enclosure 70, as depicted in FIG. 2, while two other proximal apices having coupling regions would be coupled to the slots 76c and 76d in a similar manner.

For the exemplary stent of FIG. 6, when the proximal apices having coupling regions are secured within the enclosure 70, it should be noted that the alternating proximal apices 63 without coupling regions (i.e., those terminating at the end regions 64) may be pulled radially inward in an indirect manner by the strut segments 72 and 73, which are common to adjacent apices. In this manner, all of the proximal apices of the stent 60 may be partially or fully restrained during delivery.

For illustrative purposes, it should be noted that the alternating proximal apices 63 without coupling regions (i.e., those terminating at the end regions 64) are not depicted in FIG. 2; rather, FIG. 2 depicts the presence of only proximal apices having coupling regions comprising the narrower proximal extensions 66 and the widened securement regions 67. In alternative embodiments, however, each of the proximal apices of the stent 60 may in fact be provided with such coupling regions. Moreover, in further alternatives, the coupling regions need not be located on the proximal apices, but may be positioned on other regions of the stent.

Referring still to FIG. 6, the first and second angled strut segments 72 and 73 meet with one another distally to form a distal transition region 85. In the embodiment of FIG. 6, each of the distal apices 69 comprises an end region 88 having a suture bore 89 formed therein. Further, each of the distal apices 69 comprises an imaging bore 87 adapted to receive an imaging element 87a, such as a radiopaque marker. The imaging bore 87 is disposed proximal to the suture bore 89, and the imaging bore 87 is adapted to be aligned with the proximal end 92 of the graft 90, thereby allowing the imaging element 87a associated with the imaging bore 87 to significantly enhance imaging directly at the proximal end 92 of the graft 90. Further, the stent 60 may comprises at least one barb 86 that is integrally formed along the distal transition region 85 at a location proximal to the imaging bore 87, as shown in FIG. 6.

In this manner, the stent 60 may be used as an attachment stent for endovascular graft fixation. For example, the graft material 90 may overlap with an aneurysm to seal off fluid flow into the aneurysm, while the proximal end 61 of the stent 60 may extend in a proximal direction away from the graft material, e.g., to engage a healthy portion of a vessel wall away from a diseased portion of the aneurysm. As will be apparent, one or more additional stents may be coupled to an inner or outer surface of the graft material 90, i.e., at a location distal to the stent 60, to help maintain patency throughout the graft material.

Expansion of the stent 60 is at least partly provided by the angled strut segments 72 and 73, which may be substantially parallel to one another in a compressed state, but may tend to bow outward away from one another in the expanded state shown in FIG. 6. The stent 60 may be formed from any suitable material, such as a laser-cut nitinol cannula. If manufactured from nitinol, the stent 60 may be inclined to assume the expanded state shown in FIG. 6 upon removal of a delivery sheath or engagement with the enclosure 70, as explained above.

The stent 60 has a reduced diameter delivery state so that it may be advanced to a target location within a vessel or duct. The stent 60 also has an expanded deployed state to apply a radially outward force upon at least a portion of a vessel or duct, e.g., to maintain patency within a passageway, or to hold open the lumen of a graft. In the expanded state, fluid flow is allowed through a central lumen of the stent 60. Further, the struts of the stent 60 may comprise a substantially flat wire profile or may comprise a rounded profile. As best seen in FIG. 2, the struts of the stent 60 generally comprise a flat wire profile.

The stent 60 may be manufactured from a super-elastic material. Solely by way of example, the super-elastic material may comprise a shape-memory alloy, such as a nickel titanium alloy (nitinol). If the stent 60 comprises a self-expanding material such as nitinol, the stent may be heat-set into the desired expanded state, whereby the stent 60 can assume a relaxed configuration in which it assumes the preconfigured first expanded inner diameter upon application of a certain cold or hot medium. Alternatively, the stent 60 may be made from other metals and alloys that allow the stent 60 to return to its original, expanded configuration upon deployment, without inducing a permanent strain on the material due to compression. Solely by way of example, the stent 60 may comprise other materials such as stainless steel, cobalt-chrome alloys, amorphous metals, tantalum, platinum, gold and titanium. The stent 60 also may be made from non-metallic materials, such as thermoplastics and other polymers.

In an exemplary method of use, the proximal apices 63 of the stent 60 having coupling regions are secured through the slots 76a-76d in a delivery state, as shown in FIG. 2. For example, the first proximal apex 63a may be positioned over the slot 76a, and the widened securement region 67 of the first proximal apex 63a may be aligned with, and pressed radially within, the widened proximal region 77 of the slot 76a. The proximal apex 63a may be pushed radially inward and held steady, while the cannula 30 and the auger 40 are rotated in a first direction, thereby allowing the widened securement region 67 of the proximal apex 63a to be advanced in a proximal to distal direction by the auger 40.

At this time, the widened securement region 67 is positioned within valleys 44 between adjacent helical turns 43, and the narrower proximal extension 66 extends radially through the slot 76a, as shown in FIG. 2. Notably, since the widened securement region 67 comprises the width $w_3$, which is greater than the width $W_2$ of the distal region 78 of the slot 76a, as explained above, the widened securement region 67 is captured radially within the slot 76a, despite any tendency for this portion of the stent 60 to want to self-expand radially outward. Optionally, the widened securement region 67 may comprise a concave end surface 68, as shown in FIG. 6, which may follow the contour of the valleys 44 between the helical turns 43 of the auger 40 in the delivery state.

Similarly, a second proximal apex 63b may be positioned over the slot 76b, as depicted in FIG. 2, and the widened securement region 67 may be aligned with, and pressed radially within, the widened proximal region 77 of the slot 76b, while the cannula 30 and the auger 40 are rotated in the first direction to advance the widened securement region 67 of the second proximal apex 63b in a proximal to distal direction by the auger 40. This process may be repeated until all of the proximal apices of the stent 60 having such coupling regions are secured within the enclosure 70 through the slots, in the manner shown in FIG. 2.

The coupling shown in FIG. 2 secures portions of the stent 60 within the enclosure 70 in a manner that may subsequently facilitate insertion of the subassembly comprising the cannula 30 and the stent-graft 50 into an outer sheath. As will be apparent, the outer sheath is configured to radially restrain other regions of the stent-graft 50 for delivery to a target site within a patient's anatomy, as described in the exemplary sequence below.

An introducer, similar to that described in PCT application WO98/5761, entitled "A Prosthesis and a Method and Means of Deploying a Prosthesis," which is incorporated herein by reference in its entirety, may be used to deploy the stent-graft 50. PCT application WO98/5761 describes a deployment system for an endoluminal prosthesis whereby the prosthesis is radially compressed onto a delivery catheter and is covered by an outer sheath. To deploy the system, the operator slides or retracts the outer sheath over the delivery catheter, thereby exposing the prosthesis. The prosthesis expands outwardly upon removal of the sheath. The operator can directly manipulate the sheath and the delivery catheter, which provides the operator with a relatively high degree of control during the procedure. However, in the current embodiments, trigger wires and any of their associated sleeves would not be necessary to deploy the stent-graft 50. Rather, the cannulas 30 and the auger 40 of the present embodiments may be incorporated as part of the deployment system with the stent-graft 50 being positioned coaxially between the cannula 30 and the outer sheath. A mechanism, such as a pin vise, may be employed to prevent inadvertent rotation of the cannula 30 prior to the intended rotation as described in the present application.

A wire guide may be advanced to the target site, and the cannula 30 may be advanced over the wire guide to position the apparatus 20 at the desired location in proximity to the target site, with the atraumatic tip 35 reducing the likelihood of injury to bodily passageways during delivery. The outer sheath is disposed over the cannula 30 and the stent-graft 50 during insertion to the target site. Upon proper positioning at the target site using a desired imaging modality, the outer sheath is then retracted to expose at least a portion of the stent 60. At this time, portions of the stent 60 near the proximal end 61 that are not held within the enclosure 70 may partially deploy radially outward, thereby providing an amount of slack that may facilitate subsequent longitudinal movement of the portions held within the enclosure 70.

When the stent 60 is at least partially exposed, and it is desirable to deploy the proximal end 61 of the stent 60, the cannula 30 may be rotated in a second direction, i.e., in a reverse manner from which the widened securement regions 67 were coupled within the enclosure 70. In this manner, the auger 40 is rotated in the second direction, along with the cannula 30, to thereby advance the widened securement regions 67 in a distal to proximal direction within their respective slots 76a-76d.

The proximal apices 63 of the stent 60 can self-deploy in a radially outward direction once the widened securement regions 67 are advanced proximally so that they are aligned with the widened proximal regions 67 of their respective slots 76a-76d. Notably, the angled shape of the distal region 37 of the atraumatic tip 35 may provide a ramp-like element to facilitate radial outward deployment of the widened securement regions 67. Further, the stepped surface 83, which may be positioned in the spaces in-between the slots 76a-76d, may reduce the likelihood that the proximal apices of the stent 60 become inadvertently lodged under the struts 75a-75d.

During the process of advancing the widened securement regions 67 in a distal to proximal direction within their respective slots 76a-76d, the cannula 30 and the enclosure 70 may be advanced distally. In this manner, the proximal apices 63 of the stent 60 will not be pulled proximally, relative to the remainder of the stent-graft 50, in a manner that imposes significant strain upon the proximal apices 63 during deployment. Further, as noted above, an amount of slack may be provided to portions of the stent 60 after partial pullback of an outer sheath, and such slack may further reduce strain imposed upon the proximal apices during advancement by the auger 40.

After the restrained proximal apices 63 of the stent 60 self-deploy in a radially outward direction through the proximal regions 77 of the slots 76a-76d, the remainder of the stent-graft 50 may be deployed by further retraction of the outer sheath or actuation of any other devices that are radially constraining the remainder of the stent-graft 50.

Advantageously, the proximal end 61 of the stent 60 is radially restrained without the use of convention trigger wires that span a full longitudinal length of the delivery system. Accordingly, the radial profile of the delivery system may be reduced without the provision of multiple trigger wires and one or more associated sleeves to house the trigger wires, thereby reducing packing density of the system. Moreover, deployment may be simplified as reduced deployment forces are expected to be needed relative to the use of conventional trigger wires.

As a further advantage, deployment of the stent 60 using the apparatus 20 comprising the auger 40 may allow for more precise positioning of the stent 60. In particular, deployment using the auger 40 may provide a more controlled radial release of the associated portion of the stent 60, whereas the release of conventional trigger wires may require higher deployment forces that can cause a portion of the stent to jump longitudinally, thereby potentially deploying the stent offset from the intended target site.

As yet a further advantage, during deployment of the stent 60, the enclosure 70 can rotate circumferentially relative to the atraumatic tip 35 and the cannula 30. This allows the orientation of the enclosure 70 and the proximal apices 63 to remain generally the same while the cannula 30 and the auger 40 are rotated circumferentially during deployment. Still further, the enclosure 70 encloses the auger 40 and reduces the possibility that the auger 40 can interfere with, damage, or snag various endovascular, stent or graft structures during manipulation and removal of the delivery device.

In an alternative embodiment, the axial orientation of the enclosure may be reversed, i.e., such that the widened portion of the slots 76a-76d resides at the distal end of the enclosure 70. In this alternative, the portion of the stent to be coupled within the enclosure 70 is loaded in a similar manner described above but with rotation of the cannula 30 and auger 40 in an opposite circumferential direction relative to the example of FIGS. 1-2, and further, release of the coupled portion of the stent occurs in the opposite circumferential direction that achieves this function in FIGS. 1-2.

Moreover, while one exemplary stent 60 is shown and described in FIGS. 2 and 6, various alternative stent configurations may be used in conjunction with the auger 40 and the enclosure 70 of FIGS. 1-5. Further, such stents may be deployed alone, or as part of a stent-graft system, as depicted herein.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A system for deploying at least a portion of a stent, the system comprising:
    a cannula having an outer surface;
    an auger having proximal and distal ends and a plurality of turns disposed therebetween, where the auger is coupled to the outer surface of the cannula;
    a stent having a portion dimensioned to be disposed within a valley of the auger, where rotation of the cannula and the auger advances the portion of the stent in a predetermined longitudinal direction;
    an enclosure encircling the auger, where the enclosure has a first end having a first outside dimeter and a second end having a second outside diameter, where the first outside diameter is larger than the second outside diameter,
    where the first end of the enclosure is proximal to the second end of the enclosure, and
    where the enclosure comprises a plurality of struts separated by a plurality of slots, where the portion of the stent extends through one of the plurality of slots in a delivery state.

2. The system of claim 1 where each of the plurality of struts and each of the plurality of slots are generally parallel to each other in a direction running along a longitudinal axis of the apparatus.

3. The system of claim 1 where at least one of the plurality of slots has proximal and distal regions and a width at the proximal region is greater than a width at the distal region.

4. The system of claim 3 where the stent comprises a widened securement region, where the widened securement region comprises a width that is less than a width of the proximal region of the slot and greater than a width at the distal region of the slot.

5. The system of claim 4 where the stent further comprises a proximal extension disposed adjacent to the widened securement region, where a width of the proximal extension is less than the width of the distal region of the slot.

6. The system of claim 1 where the enclosure is circumferentially rotatable relative to the cannula.

7. The system of claim 1 further comprising a distal stop member coupled to the cannula and positioned adjacent to a distal end of the enclosure, where the distal stop member allows the enclosure to rotate relative to the cannula, but prevents the enclosure from sliding distally over the cannula.

8. A system for deploying at least a portion of a stent, the system comprising:
- a cannula having an outer surface;
- an auger having proximal and distal ends and a plurality of turns disposed therebetween, where the auger is coupled to the outer surface of the cannula;
- a stent having a portion dimensioned to be disposed within a valley of the auger, where rotation of the cannula and the auger advances the portion of the stent in a predetermined longitudinal direction,
- an enclosure encircling the auger, and
- an atraumatic tip coupled to the cannula, where at least a portion of the atraumatic tip is disposed beneath the enclosure, and where the enclosure can rotate circumferentially relative to the atraumatic tip and the cannula.

9. A system for deploying at least a portion of a stent, the system comprising:
- a cannula having an outer surface;
- an auger having proximal and distal ends and a plurality of turns disposed therebetween, where the auger is coupled to the outer surface of the cannula;
- a stent having a portion dimensioned to be disposed within a valley of the auger, where rotation of the cannula and the auger advances the portion of the stent in a predetermined longitudinal direction; and
- an enclosure encircling the auger, where the enclosure comprises a plurality of struts separated by a plurality of slots, and where the portion of the stent extends through one of the plurality of slots in a delivery state.

10. The system of claim 9 where at least one of the plurality of slots has proximal and distal regions and a width at the proximal region is greater than a width at the distal region.

11. The system of claim 10 where the stent comprises a widened securement region, where the widened securement region comprises a width that is less than a width of the proximal region of the slot and greater than a width at the distal region of the slot.

12. The system of claim 11 where the stent further comprises a proximal extension disposed adjacent to the widened securement region, where a width of the proximal extension is less than the width of the distal region of the slot.

13. The system of claim 9 where the enclosure is circumferentially rotatable relative to the cannula.

* * * * *